United States Patent
Wagner et al.

(10) Patent No.: US 7,393,628 B2
(45) Date of Patent: Jul. 1, 2008

(54) METHOD FOR ENRICHING ADHERENT MONOCYTE POPULATIONS

(75) Inventors: Stephen J. Wagner, Columbia, MD (US); Andrew Myrup, Silver Spring, MD (US); Christina Celluzzi, Columbia, MD (US)

(73) Assignee: American National Red Cross, Washington, DC (US)

( * ) Notice: Subject to any disclaimer, the term of this patent is extended or adjusted under 35 U.S.C. 154(b) by 365 days.

(21) Appl. No.: 10/530,748

(22) PCT Filed: Oct. 7, 2003

(86) PCT No.: PCT/US03/31759

§ 371 (c)(1),
(2), (4) Date: Nov. 4, 2005

(87) PCT Pub. No.: WO2004/033396

PCT Pub. Date: Apr. 22, 2004

(65) Prior Publication Data

US 2006/0183103 A1    Aug. 17, 2006

Related U.S. Application Data

(60) Provisional application No. 60/416,527, filed on Oct. 8, 2002.

(51) Int. Cl.
*A01N 1/02* (2006.01)
*A61K 35/14* (2006.01)

(52) U.S. Cl. .......................................... 435/2; 424/534
(58) Field of Classification Search ....................... None
See application file for complete search history.

(56) References Cited

U.S. PATENT DOCUMENTS

| 5,665,233 | A | 9/1997 | Fukuda et al. |
| 6,120,474 | A | 9/2000 | Okuda et al. |
| 6,129,853 | A | 10/2000 | Sasayama et al. |

FOREIGN PATENT DOCUMENTS

JP    7-80062 A2    3/1995

OTHER PUBLICATIONS

Ebner et al., "Generation of large numbers of human dendritic cells from whole blood passaged through leukocyte removal filters: an alternative to standard buffy coats", J. Immunological Methods 252 : 93-104 (2001).*

* cited by examiner

*Primary Examiner*—Sandra Saucier
(74) *Attorney, Agent, or Firm*—Buchanan Ingersoll & Rooney PC

(57) ABSTRACT

The present invention provides methods and apparatus for the rapid and efficient collection and purification of activated monocytes. The methods and apparatus of the present invention provide means for effecting the collection and purification in an aseptic environment. The method involves filtering a blood component mixture through a monocyte-adhering filter; washing the blood component mixture; backflushing the filter with a physiological solution; and backflushing the filter with Dextran-40/serum albumin.

7 Claims, 3 Drawing Sheets

ALTERNATE CONFIGURATION

METHOD FOR ENRICHING ADHERENT MONOCYTE POPULATIONS

CROSS-REFERENCE TO RELATED APPLICATIONS

Figure 1:
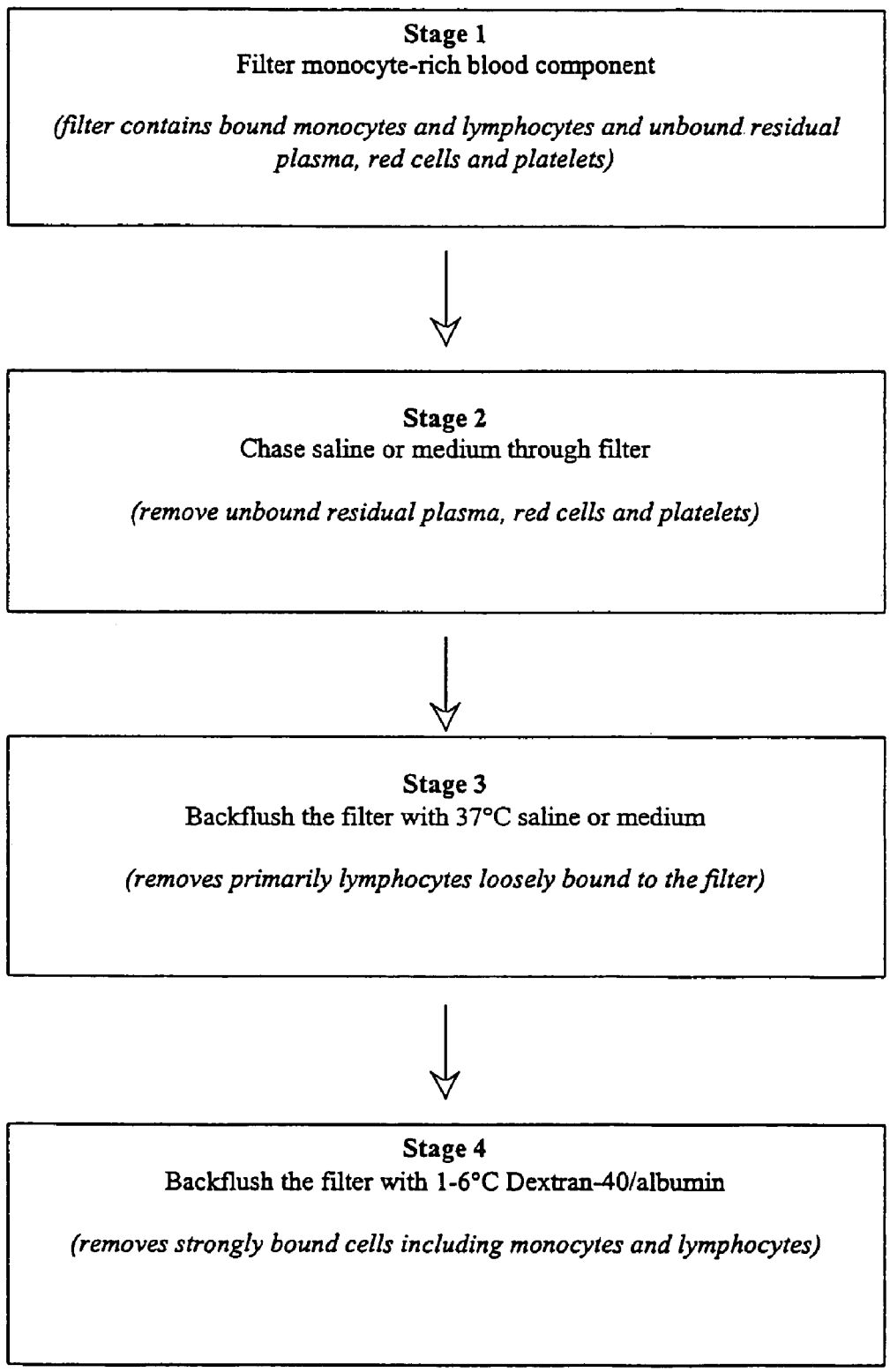

This application is a National Phase of International Application No. PCT/US03/031759, which designates the United States of America and was filed on Oct. 7, 2003, and claims priority to U.S. Provisional Application No. 60/416,527, filed on Oct. 8, 2002, the entire disclosures of which are hereby incorporated by reference.

FIELD OF THE INVENTION

The invention relates to methods and apparatus for isolating monocytes from blood using non-woven filters. The invention can be performed in a completely closed system and under aseptic conditions throughout. It is both rapid and efficient compared with existing methods. The resulting monocytes are highly activated, and demonstrate a high level of plasticity such that they can be differentiated into various lineages without the use of exogenous cytokines.

BACKGROUND OF THE INVENTION

Monocytes are an important leukocyte subset for potential clinical use as cell therapy agents. In culture, and with the addition of the appropriate cytokines, monocytes can differentiate into other clinically useful cells such as activated monocytes/macrophages (1-10), dendritic cells (11-15), endothelial-like cells (16-21), osteoclasts (22-23), and microglial cells (24). For example, monocytes/macrophages have been utilized for the experimental regeneration of central nerve tissue, the clinical treatment of chronic wounds, and adoptive immunotherapy. In animal models, monocytes/macrophages pretreated by exposure to damaged, regeneration-competent peripheral nerve imparts to macrophages the ability to promote the experimental regeneration of transected optic nerve (1) and spinal cord (2). Phytohemagglutinin stimulated allogenic mononuclear cells have been locally applied to venous or arterial ulcers in patients, resulting in accelerated granulation, epithelialization, and a greater likelihood of complete closure compared to untreated controls (3). Subcutaneous administration of allogeneic activated adherent monocytes/macrophages into the healthy tissue surrounding wounds promoted wound repair and closure in a murine system (4) and in patients with decubitus ulcers (5,6). Monocytes have also been cultured in autologous serum and recombinant granulocyte/macrophage-colony stimulating factor to promote differentiation 5 into macrophages, which have been subsequently activated with interferon gamma and other agents to produce macrophage-activated killer (MAK) cells for the treatment of cancer (7-10). Monocyte derived dendritic cells are being extensively investigated as professional antigen presenting cells and are being used in the laboratory in cellular-based vaccines for infectious diseases and are in use clinically for the treatment of cancer (11-15).

Non-Filter Methods for Monocyte Isolation:

There are several methods for the isolation of monocytes for clinical use. Large numbers ($>1\times10^9$) of highly pure monocytes (>90%) can be isolated by density gradient sedimentation followed by counterflow centrifugal elutriation of mononuclear cells collected by apheresis (25). Those cells are somewhat activated immediately following isolation, but become quiescent after overnight incubation in a defined media (26). However, no closed system elutriator has yet been developed for sterile monocyte isolation. Alternatively, large numbers of monocytes ($>1\times10^9$) can be purified by performing a continuous density gradient sedimentation to isolate mononuclear cells followed by either a continuous or discontinuous density gradient sedimentation to separate monocytes from lymphocytes (27,28). However, the technique requires two gradients, discontinuous gradients can be difficult to prepare, and the procedure is not easily carried out in closed systems. Monocytes have also been isolated by permitting attachment of cells derived from osmotically shocked buffy coats to the polyvinyl chloride polymer and plasticizers of blood containers (6). Cells isolated by adherence to blood container plastic are activated with or without osmotic shock, and have been shown to secrete pro-inflammatory cytokines during culture (29,30). While this technique can be performed in a closed system, it typically produces relatively small numbers of cells ($<5\times10^7$) compared to elutriation methods. In addition, no method for cryopreservation of adherent monocytes from osmotically shocked buffy coat has been reported. Another disadvantage is that non-filter methods are time consuming and often require more than two hours to complete the isolation procedures. Therefore, there is a clinical need for the development of methods for sterile and rapid isolation of adherent monocyte preparations containing large numbers of cells that can be cryopreserved. Such preparations would facilitate the logistics of conducting clinical trials, including dose-ranging studies. These clinical applications might include the use of monocytes/macrophages for the healing of chronic wounds, the administration of endothelial cells for healing of chronic wounds, the use of endothelial cells for supplying new vessels to support repair of damaged heart tissue, the use of dendritic cells for the preparation of infectious disease or cancer vaccines, the use of osteoclasts for the control of pathological conditions resulting in excess bone formation and atherosclerosis (31), and the use of microglial cells to remove damaged central nervous tissue.

Filter Methods for Monocyte Isolation:

One source of leukocytes from which monocytes might be derived is from non-woven filters used to deplete leukocytes from blood and blood components. For example, leukocytes, including neutrophils, eosinophils, lymphocytes and monocytes, were recovered from a leukocyte depletion filter by Chong and coworkers by backflushing with cold, anticoagulant sodium citrate solution (32). One disadvantage of such a method, however, is that many of these leukocyte reduction filters bind platelets, which are released upon backflushing the filter and thus contaminate the final product. Platelets can interfere with the further culture of monocytes to dendritic cells, osteoclasts, and endothelial cells.

Ebner and colleagues utilized blood leukocyte reduction filters as a source of leukocytes along with two additional non-filter purification processes to eventually culture monocytes into dendritic cells (33). In that study, the authors used density gradient centrifugation to remove neutrophils and T-cells rosetting with sheep erythrocytes to remove residual red cells as a means to isolate monocytes from a leukodepletion filter.

An advantage of using filters as a source of leukocytes is that large quantities of monocytes can be aseptically collected with little contamination by red cells, platelets, and plasma. Additionally, filtration methods afford especially high quantities of activated monocytes. Activated monocytes exhibit pluripotency and can be cultured and differentiated into numerous other lineages including dendritic cells, macrophages, osteoclasts, endothelial cells, and microglial cells. Activated monocytes also secrete greater quantities of cytokines associated with inflammation and differentiation. Such activated monocytes also display dendritic cell surface markers earlier during culture than monocytes collected by other methods.

Non-woven filters such as are used in cord blood filters or stem cell filters can be used to concentrate monocytes from blood component mixtures. These monocyte adhering filters preferentially bind white cells over plasma, platelets, and red cells; and preferentially bind monocytes over lymphocytes or granulocytes. Other examples of monocyte adhering filters include whole blood leukoreduction filters, which also bind white cells preferentially over plasma, platelets, and red cells. As used herein, the term monocyte-adhering filter refers to a filter that will pass about 90% of the red cells in a blood component mixture, and about 75% platelets, yet retains at least about 75 to 100% monocytes, about 20 to 80% lymphocytes, and 10 to 50% granulocytes. A blood component mixture is any mixture derived from blood or blood products that includes leukocytes, and in particular monocytes.

An example of a monocyte-adhering filter is a commercially available non-woven filter of superfine polyethylene terephthalate fibers coated with about 97% 2-hydroxyethyl methacrylate and about 3% N,N-dimethylaminoethyl methacrylate. (SCF System, Asahi Medical Corp.) (34). Such filters pass about 90% red cells and about 75% platelets, while retaining at least about 86% monocytes, about 74% lymphocytes, and about 31% granulocytes.

Using a backflush solution of Dextran-40 solution and serum albumin under high shear conditions, it is possible to recover greater than 80% of the CD34+ cells in a blood component mixture as well as about 80% of cells with long-term culture initiating cell (LTC-IC) activity. Stem cells and monocytes isolated from backflushing the filter were still contaminated with substantial numbers of lymphocytes and neutrophils; therefore, preparations still contained low percentages (10%) of monocyte subpopulations (34).

Existing filtration collection methods suffer several disadvantages. They require additional purification to adequately enrich monocytes for potential clinical use. Most, if not all, of the purification methods are difficult or impossible to carry out in a closed system, making maintenance of sterility a problem in producing clinical grade cell preparations. Similarly, most purification procedures require more than two hours for completion, making the isolation process costly and time consuming.

There is a need in the art for apparatus and methods that provide rapid means for differentially separating white cell subpopulations from the filter itself, and that avoid the need for additional separation and sterilization techniques. This would provide means for the sterile isolation of large numbers of monocytes in a closed system with adequate purity. The resulting cells could be used directly for cell therapy, or cultured in closed systems for use by those skilled in the art for differentiation into macrophages, dendritic cells, osteoclasts, endothelial-like cells, or microglial cells, and could subsequently be used in cellular therapeutic procedures.

DESCRIPTION OF PREFERRED EMBODIMENTS

The methods and apparatus of the present invention enable the selective isolation of great quantities of monocytes that are in a highly activated state. The invention further affords a rapid and efficient means for concentrating monocytes in a closed, aseptic environment. The monocyte populations resulting from the present invention possess high levels of plasticity (pluripotency) and demonstrate high rates of differentiation. Moreover, high rates of differentiation can be achieved without use of exogenous cytokines such as GM-CSF and IL-4.

The filtration process of the present invention is conducted in several stages. See FIG. 1. Those stages include: 1) filtering a blood component mixture rich in monocytes through a monocyte-adhering filter thereby binding monocytes, lymphocytes, and unbound residual plasma, red cells, and platelets; 2) chasing the blood component mixture through the filter with a physiological solution such as saline or culture medium to remove unbound residual plasma, red cells, and platelets; 3) backflushing the filter with a physiological solution such as saline or culture medium to remove loosely bound lymphocytes; and 4) backflushing the filter with a physiologically compatible viscous solution such as Dextran-40, hydroxyethyl starch, and polyethylene glycol.

As used herein, the term physiological solution means any isotonic buffer solution. Preferred examples include saline, culture medium, and the like. The physiological solution of step 3 should be above about 30° C., and is preferably about 37° C.

As used herein, the term physiologically compatible viscous solution means any natural or synthetic polymer that is physiological to cells and viscous. As used in this method, the physiologically compatible viscous solution is a vehicle for imparting high shear to the surface of the filter. Preferred examples of such solutions include Dextran-40, hydroxyethyl starch, polyethylene glycol, and the like. A particularly preferred example is a Dextran-40/albumin mixture. Preferably, the solutions used in this backflush step are chilled, and should be below about 10° C. and preferably about 1-6° C.

Figure 2:
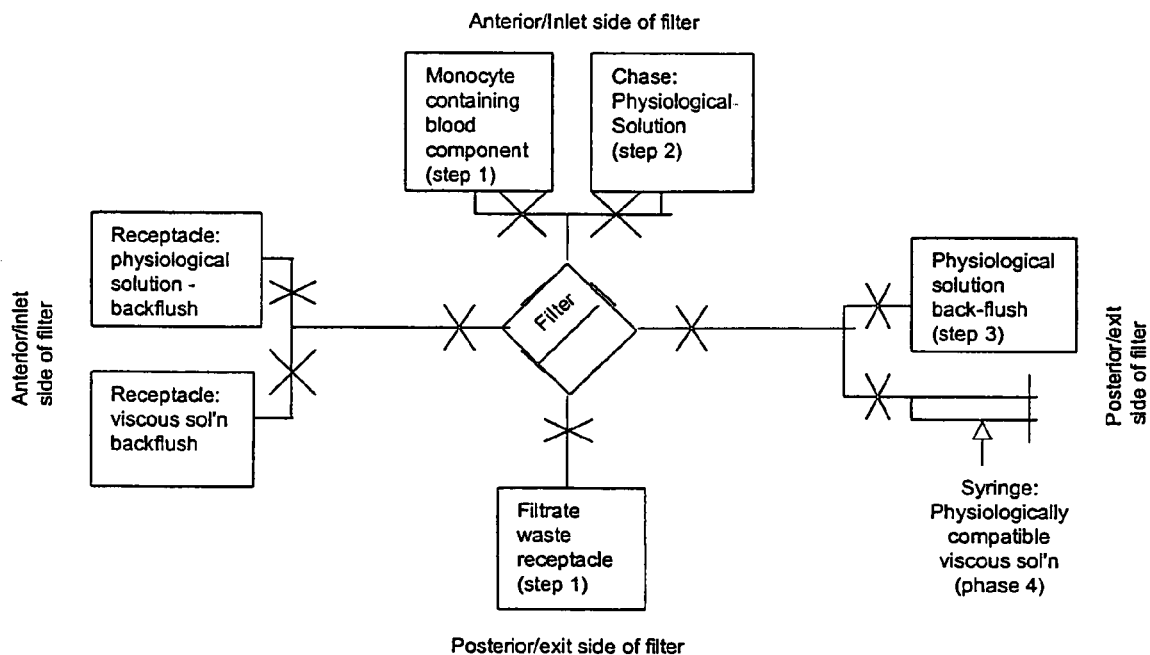
Figure 2:
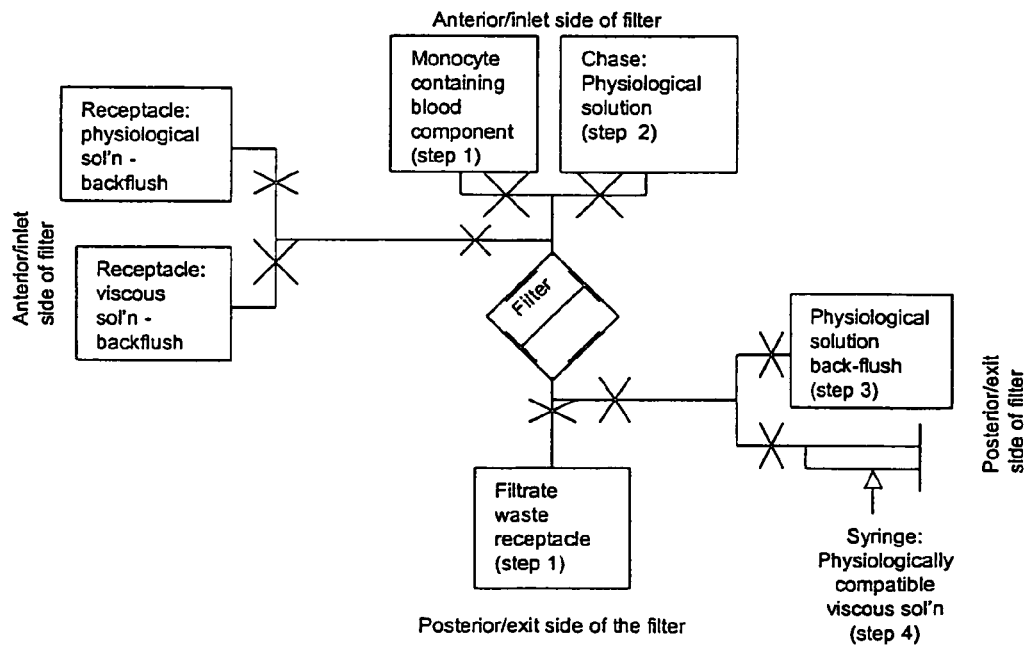

The apparatus of the present invention includes a blood filter system modified to effect the transport, filtration, and elimination of blood and other fluids entirely within a closed, aseptic system. See FIG. 2. Within the system is a chamber bisected by a non-woven monocyte-adhering filter having anterior and posterior sides. The chamber is constructed such that the two sides of the chamber are in fluid communication only through the filter itself. A biological fluid such as blood can be introduced to the portion of the chamber in facial communication with the anterior side of the filter, and the initial filtrate exits and is collected in a receptacle in fluid communication with the portion of the chamber in facial communication with the posterior side of the filter.

The system includes various air-tight fluid communication means. The fluid communication means are constructed such that they create a hermetically sealed system with the chamber enclosing the monocyte-adhering filter. The fluid communication means are further constructed with closures such as valves, stopcocks, clamps, and/or other fluid connectors that reversibly isolate the fluid communication means from the other fluid communication means and/or the chamber containing the filter.

An embodiment of the invention includes a system comprising a closed, air-tight fluid communication means for introducing a fluid, such as a biological mixture, to the anterior side of the filter; and another for removing the filtrate from the posterior side of the filter. The system optionally includes a third fluid communication means for effecting the aseptic introduction of additional fluids at the posterior side of the filter, and for applying pressure to effect backflow of such fluids from the posterior to the anterior side of the filter. The system optionally has yet another fluid communication means for removing the backflow filtrate from the anterior side of the filter.

The non-woven filter is selected such that the filter material preferentially binds monocytes over plasma, platelets, and red cells.

One preferred embodiment of the present invention provides an apparatus for effecting aseptic collection of monocytes comprising: a) a chamber bisected by a monocyte adhering filter having an anterior and posterior side; b) a first fluid communication means for introducing a fluid to the chamber on the anterior side of the filter; c) a second fluid communication means for removing a filtrate from the chamber at the posterior side of the filter; d) a third fluid communication means for introducing a fluid to the chamber at the posterior side of the filter; e) a fourth fluid communication means for removing fluid from the chamber on the anterior side of the filter; and wherein each of the fluid communication means can be independently isolated from fluid communication with the chamber and the other fluid communication means.

The use of the foregoing apparatus in the process of the present invention will now be described in more detail.

In the first step, a blood component that is rich in monocytes, such as buffy coat or cells from a mononuclear apheresis collection, is passed thru a blood filter that preferentially binds white cells over plasma, red cells, and platelets. A preferred filter is a non-woven filter such as the above-mentioned cord blood filter that binds monocytes to a greater extent than lymphocytes or granulocytes. A blood component rich in monocytes is connected to a closed tube leading to the inlet side of the filter using a sterile connecting device. The integral tubing exiting the filter joins a blood container that is used to collect the filtrate waste containing high levels of contaminating red cells, plasma, and platelets.

In the second stage, residual plasma, red cells and platelets that are retained within the filter but not bound to it, is removed by passing or chasing a physiological solution, such as saline or a defined cell medium, through the filter. The removal of unbound plasma, red cells, and platelets is important for the success of subsequent culture of the purified monocytes to other cell types. For example, monocytes are typically cultured in medium that does not contain plasma in order to avoid clotting caused by Ca++ present in media. Platelets and red cells, for example, need to be removed because they can interfere with the adherence of monocytes to polystyrene and other surfaces that is necessary for the differentiation of monocytes into dendritic cells, osteoclasts and endothelial cells. The addition of saline or defined medium in step 2 is facilitated by a bifurcation of the tubing leading to the filter and ending with a bag of saline or media or a closed, sterile seal to which saline and media can be joined using a sterile connecting device. Control of the flow of monocyte rich cell suspension or physiological chase solution is accomplished by use of clamps surrounding the tubing at the bifurcation point. The amount of saline or defined medium should range between 50 and 200 mLs with the preferred amount being 80-120 mLs.

In the third stage, primarily non-monocytic adherent cells, or lymphocytes, are removed by gently backflushing the filter with a physiological solution, such as saline, at a low shear rate and at about physiological temperature. Preferably, the physiological solution is employed in this step at about 30-40° C., and most preferably about 37° C. This backflushing step can be accomplished by having two additional tubes entering each side of the exit part of the filter, or alternatively by using tubing connected with existing tubing and valves or clamps, connected to the anterior (inlet) and posterior (outlet or exit) part of the filter, respectively. See FIG. 2. A bag of saline can be added to one of the tubes by a sterile docking device, and backflush can be initiated by gravity flow of the solution, making sure that tubing clamps are closed in the tubing leading to the filter and exiting into the waste receptacle or container. Alternatively, a backflush saline bag can be integrally connected to the filter system. In a further alternative embodiment, a syringe containing sterile saline and having tubing connected to its nozzle end can be substituted for the backflush saline bag and associated tubing.

The preferred amount of saline is 50 to 200 mLs with the optimal amount of saline backflush being 80-120 mLs. Using a syringe, the operator must take care to slowly backflush the saline through the filter. At the other end of the exit side of the filter, a tube leading to a bifurcated tube and two backflush collection: bags are used to collect the cell suspension from step 3, and in a later backflush step (step 4), the monocyte enriched fraction. Each of these bifurcation tubes contains a clamp to control fluid flow into the backflush collection bags.

In a fourth stage, primarily monocytes are removed by rapidly backflushing the filter with a cold (preferably 1-6° C.) solution of Dextran-40 and serum albumin at a high shear rate. This can be accomplished by connecting a syringe containing Dextran-40 and serum albumin solution and having a closed, sealed tubing connected to its nozzle, which can be connected to the backflush tubing using a sterile connecting device. The amount of Dextran-40/albumin solution should range between. 50 and 200 mL's, with a preferred amount being 80-120 mLs.

In summary, the above 4-step method for isolation of monocyte preparations from mononuclear apheresis units or buffy coats by filtration has several advantages over current methods, such as the potential to be carried out in a closed system, the ease of performing a simple, 4-step procedure integral to the filter, and the ability to isolate large numbers of activated monocytes ($\approx 5\times 10^8$ monocytes/$\approx 1\times 10^9$ total leukocytes) within 2 hours.

EXAMPLE 1

Monocytes were collected using a mononuclear apheresis procedure. Thirteen apheresis units were collected. Each unit contained 100 mL of approximately $5\times 10^9$ mononuclear cells and $1\times 10^9$ monocytes. Each unit was sterile docked to a cord blood collection filter (Asahi Medical Corp.) and the mononuclear suspension was allowed to pass through the filter. When 80-90% of the mononuclear suspension had passed through the filter, the filter was then gently backflushed with 50 mL of 37° C. saline twice. The filter was then strongly backflushed using 50 mL of 1-6° C. Dextran-40/albumin twice. Isolated white cells from the 1-6° C. backflush fractions were characterized for monocyte purity, monocyte recovery, viability, and phagocytosis.

Cell viability was measured by standard microscopic methods (Nikon Labophot) using a 30 μM propidium iodide/ 20 μM acridine orange stain in phosphate buffered saline.

Cell populations were determined by fluorescent microscopy using acridine orange stained cells. Cells containing ample cytoplasm and containing round, oval, notched, or horseshoe-shaped nuclei without segments were scored as monocytes, cells with plentiful cytoplasm and segmented nuclei with 2-5 lobes were scored as granulocytes, while cells with round or oval nuclei and scant cytoplasm were scored as lymphocytes.

Phagocytosis was measured by using 0.9 μm diameter yellow fluorescent beads (Pharmingen, San Diego, Calif.). Briefly, cells were centrifuged at 300×g for 10 minutes and resuspended in 20% autologous serum/RPMI (without neutral red, BioFluids, Rockville, Md.) to give $1.5\times 10^6$ leukocytes/mL. The suspension was incubated at 37° C. for 30 minutes in 5% $CO_2$/air. Following incubation, 1 mL of beads in RPMI without phenyl red (optical density: 0.6 A at 480 nm) were added, mixed, and the resulting suspension incubated at 37° C.for 1 hr. The mixture was then stained with a 54 µM acridine orange solution in RPMI, and the percentage of monocytes containing beads were scored by microscopic examination.

In Table 1, data are given regarding the characteristics of cells recovered from the Dextran-40/albumin backflushes performed at 1-6° C.

TABLE 1

| | |
|---|---|
| Total WBC from backflushed filter | $1.0 \times 10^9$ |
| Total monocytes from backflushed filter | $4.8 \times 10^8$ |
| % monocytes recovered | 43.3% |
| Monocyte purity (%) | 46% |
| Phagocytosis (%) | 48% |
| viability | 96% |

This example illustrates that high levels of viable and functional monocytes with purities approaching 50% can be isolated by the abovementioned process. This 4-step filter method recovers greater than 10-times more cells with similar purities than what is typically recovered using the osmotic shock adherence method for monocyte isolation (6).

EXAMPLE 2

Eight monocyte preparations from Example 1 were subsequently cryopreserved. A suspension of $2 \times 10^7$ monocyte/mL was added to an equal volume of cold HES/DMSO/albumin to the monocyte/macrophage preparation according to standard methods (17). Final concentrations of the cyroprotectants were 6% hydroxyethyl starch (McGaw Inc, Irvine, Calif.), 5% dimethylsulfoxide (Cryoserve, Research Industries Corp., Salt Lake, Utah), 4% human serum albumin (American Red Cross, Hyland, Calif.). One-mL aliquots were aseptically transferred to cryovials and surrounded by 1 inch styrofoam insulation and frozen in a −80° C. mechanical freezer.

Following frozen storage, cryovials were rapidly thawed in a regulated heating block at 37±3° C. for 8±1 minutes. Thawed preparations were maintained on ice until use. Thawed preparations and prefreeze preparations were analyzed for viability, phagocytosis, and monocyte purity as described in Example 1.

TABLE 2

| (% ± std dev) | Pre-freeze | 1 month frozen storage |
|---|---|---|
| Viability | 95.5 ± 5.1 | 93.4 ± 6.5 |
| Phagocytosis | 52 ± 13 | 48 ± 15 |
| Monocytes | 49 ± 12 | 42 ± 10 |

This example illustrates that monocytes isolated by the abovementioned process and be successfully cryopreserved with maintenance of viability and function.

EXAMPLE 3

Endothelial-like cells can be cultured from monocytes isolated from a cord blood filter. A monocyte preparation was isolated by filtration of an apheresis unit from Example 1. Cells were then processed according endothelial culture techniques as taught by Hebbel and colleagues (35). Cells were centrifuged and resuspended in EGM-2 medium (Clonetics) containing 5% human AB serum, and approximately $10^7$ cells were plated into a well of a cell well plate coated with either collagen or fibronectin (Becton-Dickinson). Cells were incubated at 37° C. with 5% $CO_2$. The following day, non-attached cells and medium was removed by aspiration and replaced with fresh medium. Medium was subsequently changed every one to two days.

Once cells were nearly confluent, they were passed into additional fibronectin or collagen coated wells or flasks by washing the cells with Hank's balanced salt solution twice and then incubating with 0.5× trypsin plus 1 mM EDTA for two minutes. The trypsin was neutralized by adding human AB serum to a final concentration of 20%, and subsequently 2 additional mL of EGM-2 medium. Cells were centrifuged and resuspended in EGM-2 medium and plated on additional fibronectin or collagen coated flasks.

Figure 3:
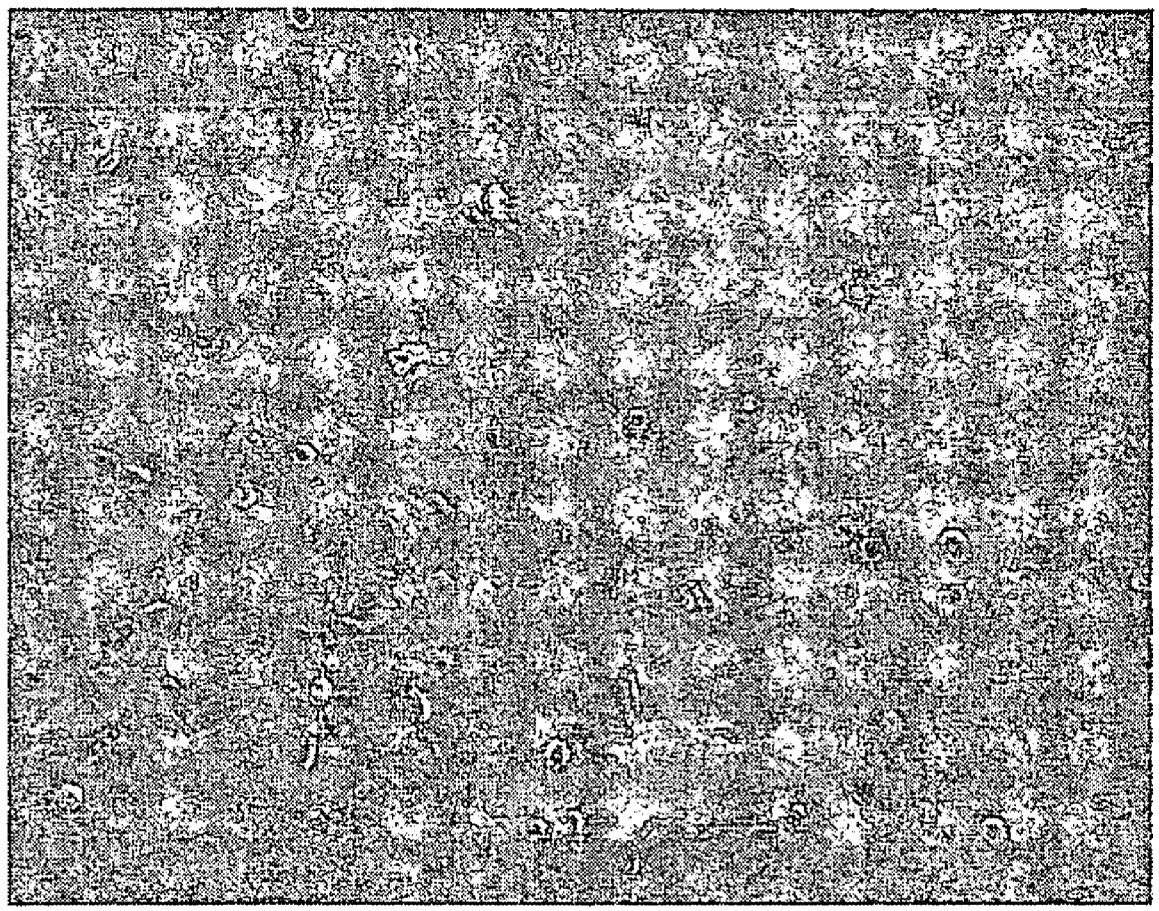

An image of cultured cells is shown in FIG. 3. The cells shown in FIG. 3 have morphologies identical to those shown by Hebble and colleagues (See Reference 35, FIG. 5). Therefore, monocytes isolated from a filter are capable of differentiating into endothelial-like cells under appropriate culture conditions.

EXAMPLE 4

Dendritic cells (DCs) can be cultured from the cells isolated from filters using the method outlined in Example 1. Monocyte preparations isolated from the filter were centrifuged and resuspended in CellGro (CellGenix, Germany) dendritic cell growth medium. Cells were placed in a 25 cm² polystyrene flask and allowed to adhere. Cell adherence was measured at 55.6±5.9%. Non-adherent cells were removed. Adherent cells were examined for their ability to develop into DCs. Cells were cultured with GM-CSF and IL4 (25 ng/mL) on day 0 and with and without TNF (30 ng/mL) on day 4. TNFα is typically added to promote DC maturation. In addition, cells were cultured in media alone to determine if the filtration process stimulated the release of cytokines capable of supporting DC differentiation or maturation. Finally, adherent cells were cultured in the absence of GM-CSF and IL4 but in the presence of TNFα.

Table 3 shows the inflammatory cytokine production of adherent cells isolated from the filter and subsequently cultured in CellGro without exogenous cytokines. Cytokines were measured by the Cytometric bead array System (BD Biosciences, San Diego, Calif.).

TABLE 3

Inflammatory cytokine production of filter-selected cells placed in media alone (pg/ml, n = 3 per timepoint, ± std dev)

| # days in media | IL6 | IL8 |
|---|---|---|
| 0 | 36 ± 51 | 351 ± 69 |
| 1 | 5,366 ± 758 | 77,349 ± 28,393 |
| 4 | 5,945 ± 2,460 | 119,575 ± 21,458 |
| 5 | 3,352 ± 4,739 | 31,024 ± 43,144 |
| 7 | 5,466 ± 2,251 | 72,304 ± 58,395 |
| 9 | 4,432 ± 1,383 | 61,010 ± 44,602 |
| (7-day ficoll-selected standard) | 121 ± 49 | 11,032 |

Filter-selected cells placed in serum-free media continue to produce very high levels of IL6 and IL8 compared to ficoll prepared control monocytes up to at least 9 days in culture (Table 3). As shown in Table 3, these levels of IL-6 and IL-8 are not produced from monocytes isolated by density gradient (ficoll) techniques. These endogenously produced cytokines, may be responsible for the differentiation of monocytes to DCs without the exogenous addition of GM-CSF and IL-4, or for the maturation of DCs with TNF-α (without GM-CSF and IL-4) to produce DCs with superior stimulation index (as seen in Table 4 below in this example).

Cultured cells were also assayed for their ability to stimulate a mixed lymphocyte reaction (MLR). DCs cultures from Example 4 were cultured with lymphocytes and assayed for $^3$H-thymidine uptake in DC-stimulated, allogeneic, dividing lymphocytes. In addition, the stimulation index for autologous DCs was determined by assaying for $^3$H-thymidine uptake of autologous dividing lymphocytes stimulated by DCs in the presence and absence of the antigen, tetanus toxin. The stimulation index is defined as the ratio of the $^3$H-thymidine uptake measured in the presence of antigen divided by $^3$H-thymidine uptake measured in the absence of antigen. Results for the mixed lymphocyte assay and the stimulation index are given in Table 4.

TABLE 4

| Added Cytokines | # days culture | n | MLR | Stimulation Index |
|---|---|---|---|---|
| GM + IL4 | 3 | 1 | 419 | 1 |
| GM + IL4 | 5 | 2 | 12,118; 9,081 | 2, 2 |
| GM + IL4 | 7 | 1 | 39,876 | 1 |
| GM + IL4 | 9 | 3 | 14,231 ± 5,129 | 9 ± 1 |
| GM + IL4 + TNFα | 7 | 2 | 20,513; 22,509 | 1, 1 |
| GM + IL4 + TNFα | 9 | 3 | 11,992 ± 3,005 | 7 ± 3 |
| No Growth Factors (NGF) | 3 | 1 | 138 | 1 |
| NGF | 5 | 2 | 9,384; 4,200 | 1, 5 |
| NGF | 7 | 1 | 12,757 | 2 |
| NGF | 9 | 2 | 4,682; 8,542 | 25, 17 |
| Only TNFα | 7 | 2 | 8,403; 20,711 | 15, 16 |
| Only TNFα | 9 | 1 | 6,673 | 63 |

These results demonstrate that DCs can be cultured from monocyte preparations isolated from a filter by a 4-stage process. Based on MLR and stimulation index results, functional DCs can be prepared without the requirement of exogenously added cytokines. This was an unexpected result. Furthermore, there is some evidence that DCs with a very high stimulation index can be prepared by culture with TNF-α, but without GM-CSF and IL-4. Again, this result was not anticipated.

REFERENCES

1. Lazarov-Spiegler O, Solomon A S, Schwartz M. Peripheral nerve-stimulated macrophages simulate a peripheral nerve-like regenerative response in rat transected optic nerve. Glial 1998; 24:329-337.
2. Rapalino O, Lazarov-Spiegler O, Agranov E, velan G J, Yoles E, Fraidakis M, Solomon A, Gepstein R, Katz A, Belkin M, Hadani M, Schwartz M. Implantation of stimulated homologous macrophages results in partial recovery of paraplegic rats. Nature Medicine 1998; 4:814-821.
3. Holzinger C, Zuckermann A, Kopp C, Schollhammer A, Imhof M, Zwolfer W, Baumgartner I, Magometschnigg H, Weissinger E, Wolner E. Treatment of non-healing skin ulcers with autologous activated mononuclear cells. Eur J Vasc Surg 1994; 8:351-6.
4. Danon D, Kowatch M A, Roth G S. Promotion of wound repair in old mice by local injection of macrophages. Proc Natl Acad Sci, USA 1989; 86:2018-2020.
5. Danon D, Frenkel O, Diamandstein L, Hashomer T, Winkler E, Orenstein A. Macrophage treatment of pressure sores in paraplegia. J Wound Care 1998; 7:281-283.
6. Danon D, Madjar J, Edinov E, Knyszynski A, Brill S, Diamantshtein L, Shinar E. Treatment of human ulcers by application of macrophages prepared from a blood unit. Exp Gerontol 1997; 32:633-41.
7. Wallace P K, Romet-Lemonne J L, Chokri M, Kasper L H, Fanger M W, Fadul C E. Production of macrophage-activated killer cells for targeting of glioblastoma cells with bispecific antibody to Fc gamma RI and the epidermal growth factor receptor. Cancer Immunol Immunother 2000; 49:493-503.
8. Boyer A, Andreu G, Romet-Lemonne J L, Fridman W H, Teillaud F L. Generation of phagocytic MAK and MAC-DC for therapeutic use: characterization and in vitro functional properties. Exp Hematol 1999; 27:751-761.
9. Hennermann B, Beckmann G, Eichelmann A, Rehm A, Andreesen R. Phase I trial of adoptive immunotherapy of cancer patients using monocyte-derived macrophages activated with interferon gamma and lipopolysaccharide. Cancer Immunol Immunother 1998; 45:250-6.
10. Andreesen R, Hennermann B. Adoptive immunotherapy with autologous macrophages: Current status and future perspectives. Pathobiol 1991; 59:259-263.
11. Banchereau J. Dendritic cells: therapeutic potentials. Transfusion Science 1997; 18:313-26.
12. Nestle F O, Alijagic S, Gilliet M, et al. Vaccination of melanoma patients with peptide- or tumor lysate-pulsed dendritic cells. Nature Medicine 1998; 4:328-32.
13. Tjoa B A, Simmons S J, Bowes V A, et al. Evaluation of phase I/II clinical trials in prostate cancer with dendritic cells and PSMA peptides. The Prostate 1998; 36:39-44.
14. Hsu F J, Benike C, Fagnoni F. Vaccination of patients with B-cell lymphoma using autologous antigen-pulsed dendritic cells. Nature Medicine 1999; 2:52-58.
15. Kugler A, Stuhler G, Walden P et al. Regression of human metastatic renal cell carcinoma after vaccination with tumor cell-dendritic cell hybrids. Nature Medicine 2000; 6:332-26.
16. Harraz M, Jiao C, Hanlon H D, et al. CD34− blood-derived human endothelial cell progenitors.
17. Schmeisser A and Strasser R H. Phenotypic overlap between hematopoietic cells with suggested angiobastic potential and vascular endothelial cells.
18. Pujol B F, Lucibello F C, Gehling U M et al. Endothelial-like cells derived from human CD14 positive monocytes. Differentiation 2000; 65:287-300.
19. Lin Y, Weisdorf D J, Solovey A, Hebbel R P. Origins of circulating endothelial cells and endothelial outgrowth from blood. J Clin Invest 2000; 105:71-77.
20. Schmeisser A, Garlichs C D, Zang H et al. Monocytes coexpress endothelial and macrophagocytic lineage markers and form cord-like structures in Matrigel under angiogenic conditions. Cardiovascular Res 2001; 49:671-680.
21. Lin Y, Chang L, Solovey A, Healey J F, Lollar P, Hebbel R P. Use of blood outgrowth endothelial cells for gene therapy for hemophilia A. Blood 2002; 99:457-62.
22. Toyosaki-Maeda T, Takano H, Tomita T, et al. Differentiation of monocytes into multinucleated giant bone-resorbing cells: two-step differentiation induced by nurse-like cells and cytokines. Arthritis Res 2001; 3:306-10.
23. Nicholson G C, Malakellis M, Collier F M, et al. Induction of osteoclasts from CD14-positive human peripheral blood mononuclear cells by receptor activator of nuclear factor kappaB ligand (RANKL). Clin Sci (Lond) 2000; 99:133-40.

24. Sievers J, Schmidtmayer J, Parwaresch R. Blood monocytes and spleen macrophages differentiate into microglia-like cells when cultured on astrocytes. Ann Anat 1994; 176:45-51.
25. Sevenson H C, Miller P, Akiyama Y, Favilla T, Beman J A, Herberman R, Stull H, Thurman G, Maluish A, Oldham R. A system of obtaining large numbers of cryopreserved human monocytes purified by leukapheresis and counter-current centrifugation elutriation (CCE). J Immunolol Meth 1983; 62:353-363.
26. Abrahamsen T G, Carter C S, Read E J, Rubin M, Goetzman H G, Lizzio E F, Lee Y L, Hanson M, Pizzo A P Hoffman T. Stimulatory effect of counterflow centrifugal elutriation in large-scale separation of peripheral blood monocytes can be reversed by storing the cells at 37° C. J Clin Apheresis 1991; 6:48-53.
27. Loos H, Blok-Schut B, van Doorn R, Hoksbergen R, Brutel de la Riviére, Meerhof L. A method for the recognition and separation of human blood monocytes on density gradients. Blood 1976; 48:731-742.
28. De Boer M, Reijneke R, van de Griend R, Loos J A, Roos D. Large-scale purification and cryopreservation of human monocytes. J Immunol Methods 1981; 225-239.
29. Frenkel O, Shani E, Ben-Bassat I, Brok-Simoni F, Shinar E, Danon D. Activation of human monocytes/macrophages by hypo-osmotic shock. Clin Exp Immunol 2001; 124: 103-109.
30. EL Kattan I, Anderson J, Yun J K, Eolton E, Yomtovian R. Correlation of cytokine elaboration with mononuclear cell adhesion to platelet storage bag plastic polymers: A pilot study. Clin and Diagnostic Lab Immunol 1999; 6:509-513.
31. Doherty T M, Uzui H, Fizpatrick L A, et al. Rationale for the role of osteoclast-like cells in arterial calcification. FASEB 2002; 16:577-582.
32. Chong C, Chen J, Roby R, Carmen R. Recovery of human leukocytes from a leukocyte depletion filter. Transfusion 1992; 32S:10S (abstract S30).
33. Ebner S, Neyer S, Hofer S, et al. Generation of large numbers of human dendritic cells from whole blood passaged through leukocyte removal filters: an alternative to standard buffy coats. J Immunol Methods 2001; 252:93-104.
34. Yasutake M, Sumita M, Terashima S, et al. Stem cell collection filter system for human placental/umbilical cord processing. Vox Sang 2001; 80:101-105.
35. Hebbel R P, Lin Y, Lollar J S. Transgenic circulating endothelial cells. PCT/US99/28033.

What is claimed is:

1. A method for isolating monocytes comprising:
   a) passing a blood component, which is enriched in monocytes compared to whole blood, through a monocyte-adhering filter,
   b) removing non-adherent cells by chasing the blood component through the filter with a physiological solution,
   c) removing loosely adherent lymphocytes by backflushing the filter with a physiological solution,
   d) removing monocytes by backflushing the filter with a physiologically compatible viscous solution, and
   e) collecting the isolated monocytes.

2. The method of claim 1 wherein the monocyte-adhering filter is a non-woven filter that passes about 90% of the red cells in the blood component mixture, and about 75% platelets, yet retains at least about 75 to 100% monocytes, about 20 to 80% leukocytes, and 10 to 50% granulocytes.

3. The method of claim 1 wherein the monocyte-adhering filter is a non-woven filter of superfine polyethylene terephthalate fibers coated with about 97% 2-hydroxyethyl methacrylate and about 3% N,N-dimethylaminoethyl methacrylate.

4. The method claim 1 wherein the physiological solutions of steps b) and c) are independently selected from the group consisting of saline and culture medium.

5. The method of claim 1 wherein the physiological solutions of steps b) and c) are at about 37° C.

6. The method of claim 1 wherein the physiologically compatible viscous solution comprises a solution selected from the group consisting of Dextran-40, hydroxyethyl starch, and polyethylene glycol.

7. The method of claim 1 wherein the viscous solution is a Dextran-40/albumin mixture at about 1-6° C.

* * * * *